United States Patent [19]
Aichinger et al.

[11] 4,027,166
[45] May 31, 1977

[54] RADIOLOGICAL MEASURING ARRANGEMENT

[75] Inventors: Horst Aichinger, Furth; Walter Sladek, Erlangen, both of Germany

[73] Assignee: Siemens Aktiengesellschaft, Berlin & Munich, Germany

[22] Filed: Apr. 21, 1975

[21] Appl. No.: 570,161

[30] Foreign Application Priority Data

May 2, 1974 Germany .......... 2421243

[52] U.S. Cl. .......... 250/416 R; 250/385
[51] Int. Cl.² .......... H05G 1/30
[58] Field of Search .......... 250/401, 402, 416, 322, 250/320, 323, 511, 385

[56] References Cited
UNITED STATES PATENTS

| 2,747,104 | 5/1956 | Jacobs | 250/401 |
| 2,796,527 | 6/1957 | Oosterkamp et al. | 250/366 |
| 3,148,276 | 9/1964 | Rothstein | 250/322 |
| 3,483,379 | 12/1969 | Brewster | 250/322 |
| 3,679,902 | 7/1972 | Hurst et al. | 250/322 |
| 3,792,267 | 2/1974 | Westerkowsky | 250/322 |
| 3,821,552 | 6/1974 | Hermeyer | 250/416 |
| 3,875,411 | 4/1975 | Kunert | 250/416 |
| 3,942,012 | 3/1976 | Boux | 250/385 |

Primary Examiner—Alfred E. Smith
Assistant Examiner—B. C. Anderson
Attorney, Agent, or Firm—Hill, Gross, Simpson, Van Santen, Steadman, Chiara & Simpson

[57] ABSTRACT

A radiological measuring arrangement having first and second X-ray measurement fields wherein both X-ray beam measurement fields or areas are located concentrically with respect to each other in one plane, and that for the generation of a signal corresponding to the formation of the surface dosage product there are present means for forming the sum of the output signals of the two beam measurement fields. In the inventive measuring arrangement in order to encompass two magnitudes, namely, the surface dosage product and the incidence dosage, only a single beam measurement element need be applied to the diaphragm housing of an X-ray tube. A time measuring device or chronometer may be provided at the output of the second measurement field. In this further construction it becomes possible, in addition to the surface dosage product on the incidence dosage, to also obtain the transillumination time for X-ray exposures.

5 Claims, 2 Drawing Figures

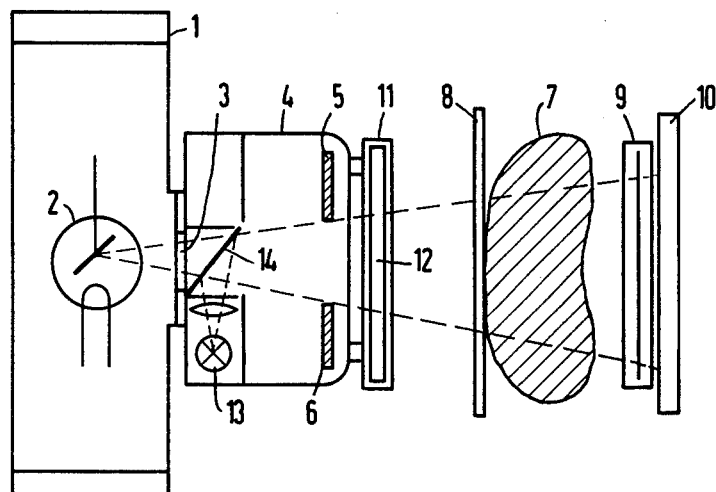
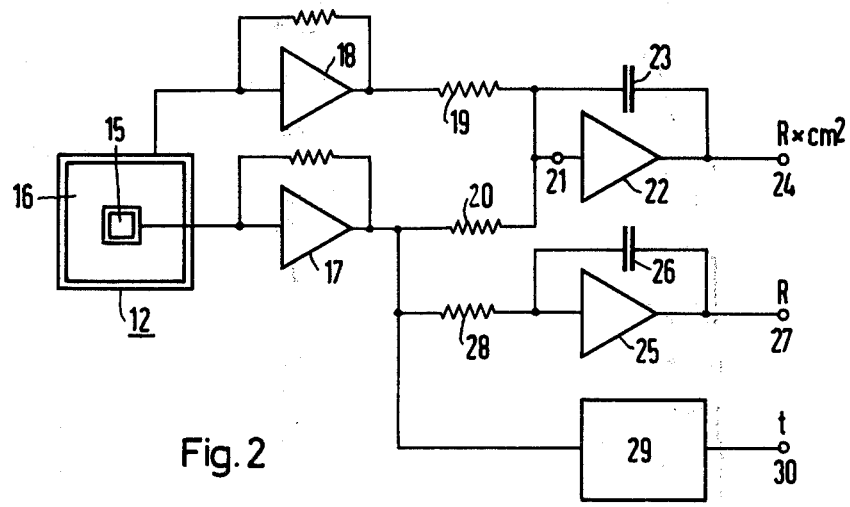

4,027,166

RADIOLOGICAL MEASURING ARRANGEMENT

FIELD OF THE INVENTION

The present invention relates to a radiological or commercial X-ray measuring arrangement.

DISCUSSION OF THE PRIOR ART

A radiological measuring arrangement for detection of the X-ray dosage load application to a patient having a first measurement field which is located on the diaphragm or optical focusing housing of an X-ray tube, and which is selected to be so large so as to, even at maximum beam field size, encompass the entire X-radiation emanating from the primary beam diaphragm, and whose portion which is passed through by the X-radiation corresponds to the currently focused beam field size, and forms a signal in conformance with the surface dosage product, and including a second beam measurement field located on the diaphragm housing which is fully passed through by the X-radiation even at the smallest beam field size and delivers a signal conforming to the incidence dosage, is known from the periodical "Rontgenblatter", Volume 12, 1959, pages 244 through 256. In this known measuring arrangement it is possible that the surface dosage product be obtained in X-rays × cm$^2$, as well as the incidence dosage in X-rays. For obtention of the surface dosage product, an X-ray beam measuring chamber is located at the beam outlet side of the diaphragm housing of the X-ray tube, whose size is so selected that, even at maximum beam field size, there is encompassed the entire X-radiation emanating from the primary beam diaphragm. The signal which is delivered from this X-ray beam measuring chamber is transmitted to an indicator arrangement. For the detection of the incoming or incidence dosage, a second beam measuring chamber is located at the inlet side of the diaphragm or optical focusing housing, whose outlet signal is independent of the focused radiation field.

Of disadvantage in the known measuring arrangement is the fact that two mutually separate X-ray measuring chambers are located at two different locations of the diaphragm housing for the X-radiation.

SUMMARY OF THE INVENTION

Accordingly, it is an object of the present invention to provide a radiological or commercial X-ray measuring arrangement of the above-described type, which is simplified in comparison with the current state of the technology.

The foregoing object is inventively achieved in that both X-ray beam measurement fields or areas are located concentrically with respect to each other in one plane, and that for the generation of a signal corresponding to the formation of the surface dosage product there are present means for forming the sum of the output signals of the two beam measurement fields. In the inventive measuring arrangement in order to encompass two magnitudes, namely, the surface dosage product and the incidence dosage, only a single beam measurement element need be applied to the diaphragm housing.

An advantageous further feature of the invention is obtained by providing a time measuring device or chronometer at the output of the second measurement field. In this further construction it becomes possible, in addition to the surface dosage product on the incidence dosage, to also obtain the transillumination time for X-ray exposures.

BRIEF DESCRIPTION OF THE DRAWINGS

Further advantages and details of the invention may now be ascertained from the following description of an exemplary embodiment thereof, taken in conjunction with the accompanying drawing; in which:

FIG. 1 generally diagrammatically illustrates a radiological measuring arrangement constructed pursuant to the present invention in connection with the therewith associated components of an X-ray diagnostic installation; and FIG. 2 shows a circuit diagram of the measuring arrangement with the therewith associated circuitry elements.

DETAILED DESCRIPTION

In FIG. 1 of the drawing there is illustrated a housing 1 within which there is located an X-ray tube 2, the latter of which is supplied with high-voltage and filament current from a suitable X-ray generator (not shown). The X-radiation exits from the housing 1 through a beam outlet aperature or window 3 and transverses a diaphragm or focusing housing 4, in which diaphragm plates 5 and 6 are schematically illustrated, and which focus in the radiation area or field of a patient 7, who lies on a support platform 8. The X-radiation, after penetrating through the patient 7, traverses an X-ray measurement chamber 9 of an automatic exposure timer and then enters into a cassette 10 within which there lies an X-ray film.

In FIG. 1 there may be ascertained only two diaphragm or focusing plates 5 and 6, which limit the X-radiation in one direction. In a similar manner, limiting or restricting the X-radiation in a direction perpendicular thereto, is carried out through two further diaphragm plates.

At the outlet of the diaphragm housing 4 there is fastened a housing 11, within which there is located an X-ray measurement chamber 12.

For completeness' sake, in FIG. 1 there is also illustrated a light visor which serves for the restriction of the focused radiation field. This light visor receives a light source 13 in the diaphragm housing 4 which beams through a lens and across a mirror 14 from the outlet aperture of the diaphragm housing 4. The mirror 14 is pervious to X-rays.

From FIG. 2 there may be ascertained that the X-ray measuring element or chamber 12 consists of two beam measurement fields or areas 15 and 16 which are located concentrically to each other in one plane. The measurement field 15 is so dimensioned that even at the narrowest focusing it still lies completely within the cone of the beam. In contrast therewith, the measurement field 16 is so dimensioned that at the largest focusing it still encompasses the enitre X-radiation emanating from the primary beam focusing diaphragm, and that the portion which is passed through by the X-radiation always conforms to the currently focused X-ray field size. For example, the measurement fields or detectors 15 and 16 may be constructed as shown in U.S. Pat. Nos. 2,796,527, and 2,747,104; particularly from plates, as shown in FIGS. 2 and 3 of U.S. Pat No. 2,747,104, in which the one plate has a central aperture within which there is positioned the second plate. Naturally, within the scope of the invention, it is also possible to employ other detectors, such as ionization chambers, or the like.

The output signal of the measurement field 15 is amplified in an amplifier 17, and the output signal of the measurement field 16 in an amplifier 18. The amplified output signals are transmitted through two coupling resistances 19 and 20 to the input 21 of an amplifier 22 which operates in conjunction with a condenser 23 acting as an integrator. At the input 21, these two signals are then added. A signal lies at the input 21, which depends upon the dosage output and the focused field size. After integration of this signal in the elements 22, 23, a signal is located at output 24, which characterizes the surface dosage product.

The output signal of the amplifier 17 depends upon the current dosage output, but not upon the size of the focused field. Thus upon amplification in amplifier 25, which has an integrating condenser 26 associated therewith, a signal is present at the output 27, based upon which there may be determined the incidence dosage. The integration circuit 25, 26 is connected to the output of the amplifier 17 through a coupling resistance 28.

Thereby, the output signal of the amplifier 17 depends only upon the dosage output and not upon the focused field size, inasmuch as the measurement field 15, even at the smallest focusing, is still fully passed through by the X-radiation. The output signal of the amplifier 17 also controls a time measuring device or chronometer 29, which is started up at the appearance of X-rays, and delivers a signal at its output 30 which characterizes the time during which the X-radiation occurs, namely the exposure or transillumination time.

The signals at the outputs 24, 27 and 30 may control indicator instruments for indication of the magnitudes of the surface dosage product, incidence dosage and transillumination.

It is essential to the invention that the measurement fields 15 and 16 lie concentrically with respect to each other within a single plane, meaning being located within a common housing (11 in FIG. 1) so that the construction of the measuring arrangement is essentially simplified in comparison with the present state of the technology.

The output signal at output 27, precisely considered, presents the focus outlet dosage. The incidence dosage may thereby be obtained through recalculation to the focus-object distance. This recalculation may be carried out, for example, with the aid of a curve. At a fixedly pregiven focus-object distance this may then be evaluated in a further connected measurement amplifier to which there is transmitted the signal in the conductor 27.

The amplifiers 17 and 18 operate as current-voltage transducers in the embodiment according to FIG. 2. Their output voltages are proportional to the ionization flows or currents of the measurement fields 15 and 16.

After completion of an exposure, the time measuring device or chronometer 29 must once again be switched back into its zero condition. Furthermore, the integrators 22, 23 as well as 25 and 26, must be deactivated. The return switching and deactivation may be effected either manually or automatically, when the output signals of the measuring arrangement have been utilized.

While there has been shown what is considered to be the preferred embodiment of the invention, it will be obvious that modifications may be made which come within the scope of the disclosure of the specification.

What is claimed is:

1. In a radiological measuring arrangement for the X-ray dosage load applied to a patient, including an X-ray tube having a focusing diaphragm housing; a first measurement field arranged on said housing, said field being selected to be so large to encompass the entire X-radiation emanating from the primary beam focus even at a maximum beam field size, and of which the portion transversed by the X-radiation conforms to the currently focused beam field size, and including means for forming a signal corresponding to the surface dosage product; and a second beam measurement field adapted to be fully traversed by the X-radiation at even the smallest beam field size and including means for forming a signal corresponding to the incidence dosage, the improvement comprising: said first and second beam measurement field lying concentrically to each other in one plane; and means for forming a signal corresponding to the surface dosage product from producing the sum of the output signals of the first and second beam measurement fields, said surface dosage product being the product of the X-ray dosage obtained by said first and second measurement fields and the surface of said measurement field subjected to said X-radiation.

2. An arrangement as claimed in claim 1, comprising an electrical integrator connected to said sum-producing signal forming means.

3. An arrangement as claimed in claim 1, comprising an electrical integrator for receiving the output signal of said second beam measurement field.

4. An arrangement as claimed in claim 1, comprising time measuring means being connected to the output of one of said measurement fields for determining the examination time for said patient.

5. An arrangement as claimed in claim 4, said time measuring means being connected to the output of the second measurement field.

* * * * *